United States Patent
Bell

(10) Patent No.: US 11,833,304 B2
(45) Date of Patent: *Dec. 5, 2023

(54) PATIENT VENTILATOR CONTROL USING CONSTANT FLOW AND BREATHING TRIGGERS

(71) Applicant: Adam D. Bell, Phoenix, AZ (US)

(72) Inventor: Adam D. Bell, Phoenix, AZ (US)

(73) Assignee: Levered Impact, LLC, Phoenix, AZ (US)

( * ) Notice: Subject to any disclaimer, the term of this patent is extended or adjusted under 35 U.S.C. 154(b) by 452 days.

This patent is subject to a terminal disclaimer.

(21) Appl. No.: 17/196,434

(22) Filed: Mar. 9, 2021

(65) Prior Publication Data
US 2021/0402119 A1    Dec. 30, 2021

Related U.S. Application Data

(62) Division of application No. 16/917,055, filed on Jun. 30, 2020, now Pat. No. 10,980,954.

(51) Int. Cl.
*A61M 16/00* (2006.01)
*A61M 16/04* (2006.01)
*A61M 16/20* (2006.01)

(52) U.S. Cl.
CPC ...... *A61M 16/024* (2017.08); *A61M 16/0003* (2014.02); *A61M 16/0051* (2013.01);
(Continued)

(58) Field of Classification Search
CPC ............ A61M 16/024; A61M 16/0003; A61M 16/0051; A61M 16/0402; A61M 16/0468; A61M 16/0486; A61M 16/204; A61M 16/205; A61M 2016/0039; A61M 2016/0042; A61M 2205/3334; A61M 2205/3337; A61M 2205/3344; A61M 2205/3382; A61M 2205/3386; A61M 2205/502; A61M 11/00; A61M 16/0063; A61M 16/01; A61M 16/0427; A61M 16/0465; A61M 16/12; A61M 16/14;
(Continued)

(56) References Cited

U.S. PATENT DOCUMENTS 3,946,729 A    3/1976    Hanna
4,227,523 A    10/1980   Warnow
(Continued)

OTHER PUBLICATIONS

Minhas, J. S. et al., "PaCO2 measurement in cerebral haemodynamics: face mask or nasal cannulae?", Physiological measurement, 38(7):101 (Jun. 22, 2017).
(Continued)

*Primary Examiner* — Victoria Murphy
(74) *Attorney, Agent, or Firm* — BOOTH UDALL FULLER, PLC; Bryce W. Burnham

(57) ABSTRACT

The embodied invention is a new inspiration/expiration ventilator flow design, with a constant inspiration flow and intermittent-concurrent expiratory flow based on lung pressure setpoints. This mode is possible by using a new dual lumen tube inserted into a patient Trachea. Additionally, the control provides support for patient initiated breathing which is initiated by a lung pressure drop. This control provides continuous and gentle recruitment of lung alveoli.

18 Claims, 14 Drawing Sheets

(52) U.S. Cl.
CPC .... *A61M 16/0402* (2014.02); *A61M 16/0468* (2013.01); *A61M 16/0486* (2014.02); *A61M 16/204* (2014.02); *A61M 16/205* (2014.02); *A61M 2016/0039* (2013.01); *A61M 2016/0042* (2013.01); *A61M 2205/3334* (2013.01); *A61M 2205/3337* (2013.01); *A61M 2205/3344* (2013.01); *A61M 2205/3382* (2013.01); *A61M 2205/3386* (2013.01); *A61M 2205/502* (2013.01)

(58) Field of Classification Search
CPC .. A61M 2016/0024; A61M 2016/0027; A61M 2202/0208; A61M 2202/0225; A61M 2202/0275; A61M 2202/0468; A61M 2205/18; A61M 2205/505; A61M 2205/8206; A61M 16/042; A61M 16/0434; A61M 16/0833; A61M 2209/084; A61M 2210/1039; A61M 2230/432

See application file for complete search history.

(56) References Cited

U.S. PATENT DOCUMENTS

| | | | | |
|---|---|---|---|---|
| 4,421,113 | A | * | 12/1983 | Gedeon ............... A61M 16/024 128/204.23 |
| 4,502,481 | A | | 3/1985 | Christian |
| 4,646,733 | A | * | 3/1987 | Stroh ................ A61M 16/042 128/207.14 |
| 5,107,831 | A | | 4/1992 | Halpern |
| 5,127,400 | A | | 7/1992 | Devries |
| 5,161,525 | A | | 11/1992 | Kimm |
| 5,167,622 | A | | 12/1992 | Muto |
| 5,315,989 | A | | 5/1994 | Tobia |
| 5,692,497 | A | | 12/1997 | Schnitzer |
| 5,931,160 | A | | 8/1999 | Gilmore |
| 5,954,050 | A | | 9/1999 | Christopher |
| 6,000,396 | A | | 12/1999 | Melker |
| 6,158,432 | A | | 12/2000 | Biondi |
| 6,584,973 | B1 | | 7/2003 | Biondi |
| 10,980,954 | B1 | | 4/2021 | Bell |
| 2005/0121033 | A1 | | 6/2005 | Starr |
| 2009/0151719 | A1 | | 6/2009 | Wondka |
| 2009/0241957 | A1 | | 10/2009 | Baker, Jr. |
| 2015/0083135 | A1 | * | 3/2015 | Cheng ............... A61M 16/0051 128/204.23 |
| 2016/0213870 | A1 | | 7/2016 | Kumar |

OTHER PUBLICATIONS

Patel, N. et al., "The Leicester cerebral haemodynamics database: normative values and the influence of age and sex", Physiological measurement, 37(9):1485-1498 (Sep. 2016).
VentilatorManual_Maquet.pdf.

* cited by examiner

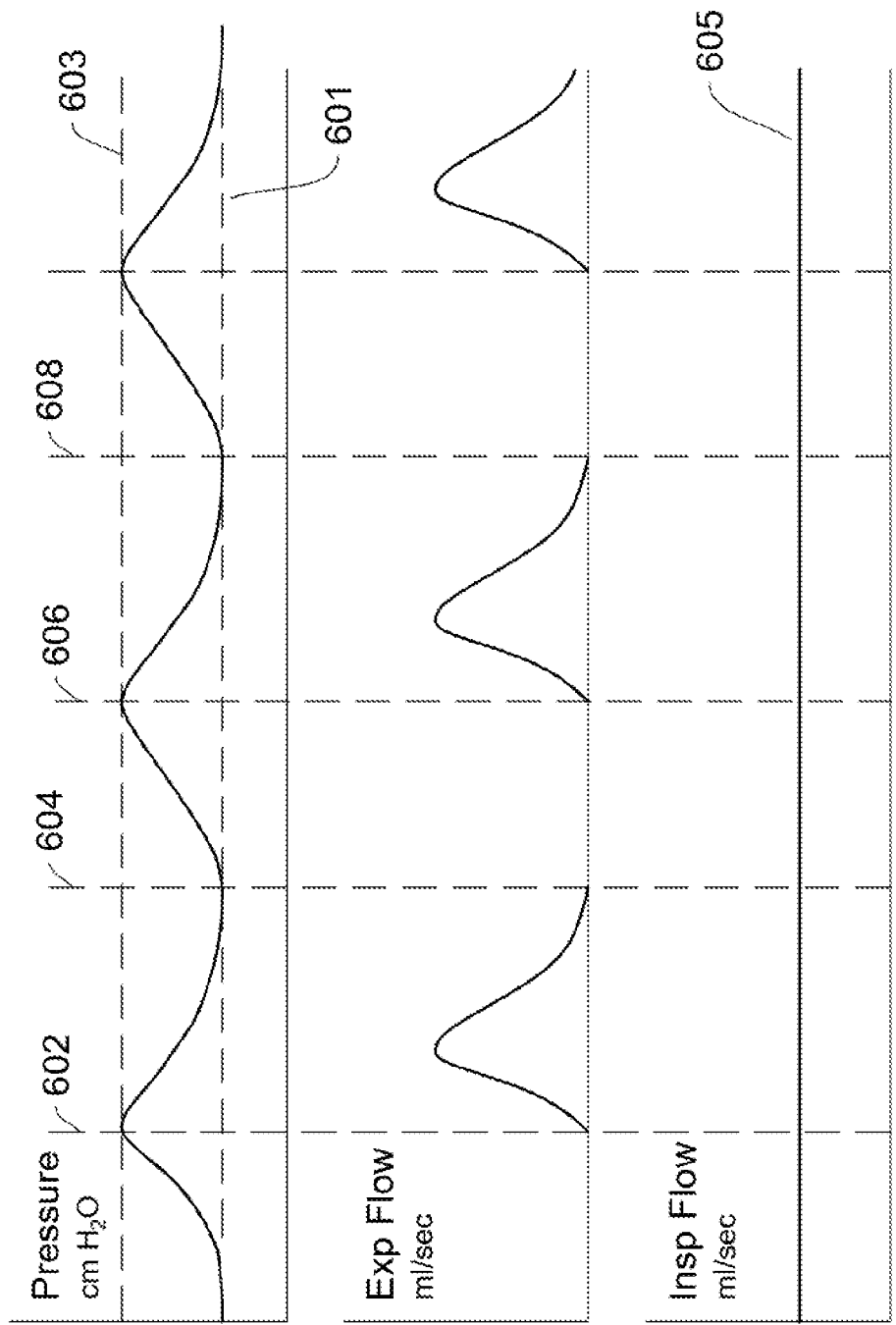

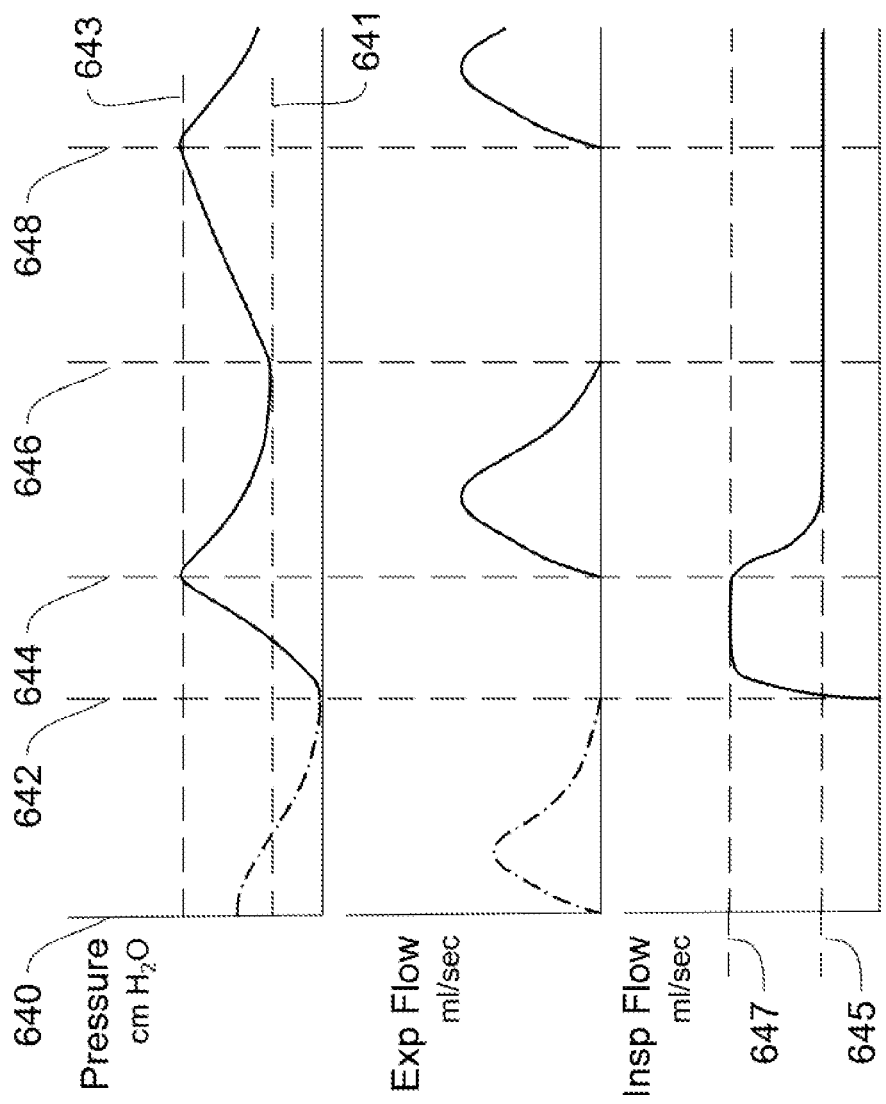

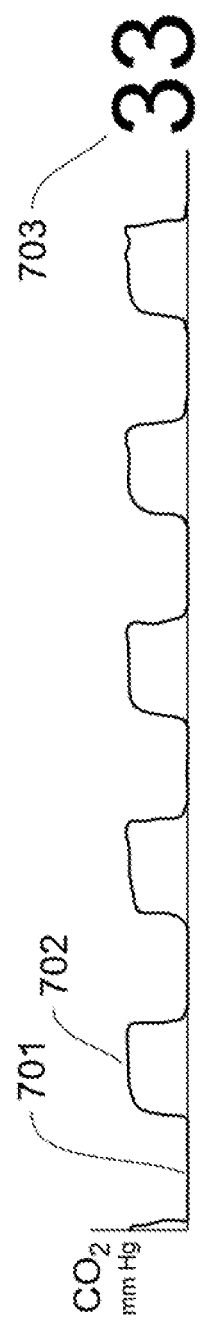

PATIENT VENTILATOR CONTROL USING CONSTANT FLOW AND BREATHING TRIGGERS

CROSS REFERENCE TO RELATED APPLICATIONS

This application is a divisional application of U.S. patent application Ser. No. 16/917,055 filed on Jun. 30, 2020. The entire prior application is incorporated by reference herein.

STATEMENT REGARDING FEDERALLY SPONSORED RESEARCH OR DEVELOPMENT

Not applicable.

REFERENCE TO SEQUENCE LISTING, A TABLE, OR COMPUTER PROGRAM LISTING

Not applicable.

BACKGROUND OF THE INVENTION

(1) Field of the Invention

This invention is directed to improved methods of ventilating lungs, where positive pressure is utilized to curate continuous gas flow and thus provide the needed oxygen when a patient cannot sufficiently and regularly self-inflate their lungs.

(2) Description of Related Art

Acute Respiratory Distress Syndrome (ARDS) occurs in about 16% of ventilated adult patients in an intensive care unit (ICU) and can carry a mortality rate of up to 45%. In ARDS, a large percentage of the lung is collapsed. Aggressive therapy technologies, including high frequency oscillating ventilation (HFOV) and airway pressure release ventilation (APRV), have not solved this issue. Neither can be used without concern for negative sequelae. During general surgery, CT scans consistently show dependent lung collapse within a few minutes after applying anesthesia.

Emerging science pertaining to the pathophysiology of covid-19 suggests that while some COVID patients do go into ARDS, others suffer from regional pulmonary vasoconstriction. This causes a lack of blood flow to and from alveoli as compared to normal lung function. Traditional ARDSnet style ventilation, which is the default ICU method, has not shown benefit, and may create a compounding tamponade effect on pulmonary vasculature with covid-19 pathophysiology. A gentler ventilatory mode would likely be of benefit in the setting of such pathophysiology.

Biomimicry is the design and production of materials, structures, and systems that are modeled on biological entities and processes. It is a rigorous, nonlinear innovation methodology, where nature's principles are used to sustainably meet challenges of design, engineering, ethics, and process. It can be utilized to solve and resolve issues related to lung function and ventilation problems.

Improvements in ventilation are important. In 2016 the U.S. alone had 5,534 hospitals, most have at least one ICU, many have 4-6 ICUs accommodating 5-20 beds each. All of these hospitals need appropriate methods of ventilating patients.

Typically, ARDS occurs 2.2 times per year per intensive care unit (ICU) bed. Further, it will occur in 16.1% percent in ventilated patients who are admitted for more than 4 hours (per Brun, 2004) and despite current methods of ventilation there is still a mortality rate between 25% and 43%. An analysis identifies underlying pathologic mechanisms, comorbidities, and population types. It is safe to say that the standard of care in mechanical ventilation, may itself contribute to a high failure rate, and resultant deaths. These statistics ignore a potential morbidity among survivors who may suffer chronic and intractable fibrotic changes to their lung parenchyma. Indeed, the problem has not yet been solved.

BRIEF SUMMARY OF THE INVENTION

The conceived invention is a new inspiration/expiration flow design that is a biomimetic flow-based mode, with expiratory flows primarily created by lung pressure set points. It avoids or severely limits barotrauma, volutrauma, atelectrauma and, extremes of arterial $CO_2$ when compared to existing ventilators. This mode is possible by using a new multi-tube airway inserted into a patient's endotracheal tube. The new airway system allows a continuous inspiratory flow along with periodic concurrent expiratory flows. Both flows are compliance dependent and pressure responsive, and avoid previous difficulties seen with other modes of mechanical ventilation.

BRIEF DESCRIPTION OF THE SEVERAL VIEWS OF THE DRAWING(S)

FIG. 6A-6D show graphs of lung pressure and flow for a breathing patient, and for a continuous ventilatory flow without spontaneous breathing.

FIG. 7 shows a Capnographic Waveform for a typical breathing patient and for a constant inspiratory flow.

DETAILED DESCRIPTION OF THE INVENTION

Figure 1:
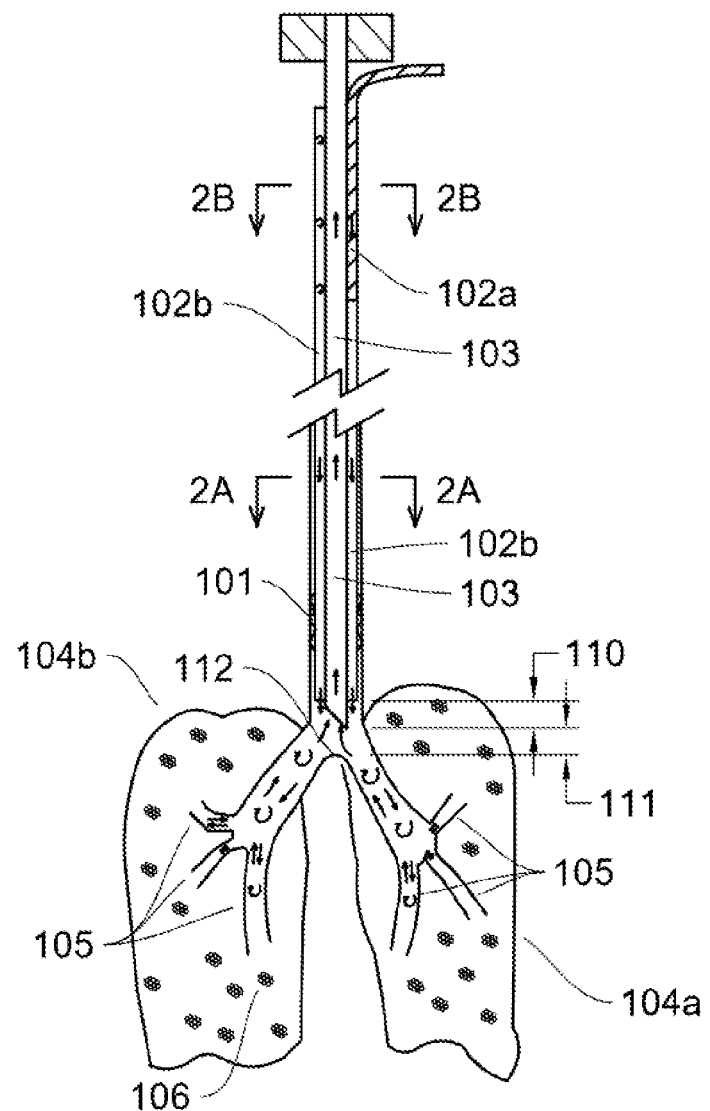
FIG. 1 shows an illustration of ventilating tubes when installed in the airway of a patient.

Basic Ventilatory Mechanics, Modes, Physiology, and Related Context

This invention is an improved method of ventilating lungs, using a novel default mode which offers continuous inspiratory flow (inflation via positive pressure ventilation) with intermittent concurrent expiratory flow (passive exhalation). In contrast to traditional ventilatory modes, where inspiration and exhalation must occur only at separate times without temporal overlap and so can never occur together but only in sequence, this mode seeks to offer continuous gentle recruitment (opening up) of functional anatomical lung units (alveoli).

Ventilation is the movement of gases into and out of the lungs. When terrestrial mammals, including humans, are in a healthy state, breathing is the result of autonomic mechanisms or conscious intent. Either way, a diaphragm contraction is triggered which leads to larger cavity size in the chest. This results in a low lung pressure as compared to atmospheric pressure. This allows air to flow into the lungs and is called "negative pressure ventilation."

When the diaphragm then relaxes, it does so in a direction which decreases the volume of the chest back to the previous baseline. This increases the intrathoracic pressure above atmospheric pressure and exhalation results. Terrestrial mammals breathe based on tidal ventilation. Tidal volume times breaths per minute yields minute ventilation (amount of air moved in a minute).

Respiration is a process of molecular exchange, largely by diffusion, which occurs at the alveolar-capillary bed level (e.g. $O_2$ rich gas mixtures go in, metabolism occurs, and $CO_2$ rich gas mixtures become available for exhalation). The normal partial pressure of $CO_2$ in human arterial blood ($PaCO_2$) is 35-45 mmHg. Without sufficient ventilation and respiration both atelectasis (alveolar collapse) and acidosis secondary to $CO_2$ build-up (hypercapnia [$PaCO_2$>45 mmHg]) occur. Carbon dioxide can therefore be thought of as a source of acid in humans: ([$CO_2$+ $H_2O$]↔$H_2CO_3$↔[$HCO_2$_+H+]). The normal pH range for humans is 7.35-7.45 and a pH<7.2 is associated with grave disease states and metabolic dysfunction as many common metabolic reactions, including those involving vasoactive agents such as epinephrine and noradrenaline, are negatively impacted.

Positive pressure ventilation (PPV) is the basis for most existing ventilators. Today, mechanically ventilated patients usually have single-lumen airway tubes inserted into their tracheas through which air is moved in a closed circuit (ventilator, tube, bronchi, and lungs). In tidal ventilation, that is a sequence of inspiration and exhalation without temporal overlap of the two. PPV is accomplished when the pressure generated by a ventilator exceeds the pressure in the lungs thus causing inspiratory airflow and resultant inflation of the lungs. When positive pressure is stopped, the lungs naturally recoil and start to collapse until they reach an internal pressure state equal to that of the ventilator circuit. Depending on the ventilator mode, levels of sedation, and the patient's innate state, a given patient may be either apneic without the ventilator's help or may breathe spontaneously, based on diaphragmatic movement, in addition to ventilator-initiated breaths. Most modern ventilation systems detect pressure changes that come from diaphragmatic motion and then initiate a breath based on such "demand" by the patient in addition to other breaths they are set to give. Such positive pressure in addition to negative pressure generated by the patient helps the patient overcome resistance inherent in the ventilator circuit relative to ambient air.

Flow, in the setting of positive pressure mechanical ventilation, is the rate at which gases are pushed into the lung. Breath volume, rate, lung compliance (i.e. distensibility and elastic recoil [Cdyn=tidal volume/A Pressure]) and inspiratory phase duration all impact flow. Cycle time in ventilation can be determined by dividing the seconds per minute by the breaths per minute. For example, at a rate of 12 breaths per minute, 5 seconds are allotted for each breath, which includes both the inspiratory and expiratory phases, whereas at a rate of 30, only 2 seconds would be allotted per breath. Flow per unit time can, therefore, be calculated if the volume per breath and the duration of the inspiratory phase are known. For example, with 600 ml/breath and an inspiratory phase of one second, the flow rate is 600 ml/sec, whereas at 600 ml/breath with an inspiratory time of 3 seconds, the flow rate is 200 ml/sec.

Air takes the path of least resistance in filling a lung, usually into open air passages and open sacs (recruited alveoli). To re-open, or recruit, an atelectatic alveolus, one must ventilate it such that a "critical opening pressure" is exceeded. The analog of a balloon is useful here. When you blow up a balloon, a little bit of air enters with very little pressure, but soon, much more pressure is needed to overcome a threshold after which the balloon inflates towards maximum with relative ease. It is the same with the alveolus. If opening pressures are continuously exceeded, alveolar segments will be recruited. When pressures drop below opening thresholds for extended periods, without sufficient residual aeration, atelectasis can result.

When inspiratory duration to volume ratios (Id:V) are low (i.e. short times and larger volumes) flow rates are higher than when Id:V ratios are lower. When flow rates are higher, gas distribution within the lung is more heterogeneous with gas moving to already aerated areas more readily, resulting in local overdistension and volutrauma, while other regions remain poorly aerated. This problem is exacerbated in disease states. When flow rates are lower a more homogenous distribution of gases can be observed throughout the lungs with a concurrent increase in the removal of $CO_2$ at a given metabolic rate and minute volume. Thus, the curation of a low-flow state in the setting of sufficient minute volume can be beneficial as it minimizes volutrauma, mitigates hypercapnic acidosis, and promotes aeration.

Positive end expiratory pressure (PEEP) is the result of incomplete lung emptying. In healthy states the lungs do retain some residual volume on end expiration, and that volume yields some pressure. This pressure has a stenting effect such that more alveolar units which were already open, remain so, as compared to states without PEEP when expiration occurs. Normal physiologic PEEP in humans is the subject of some debate, but the current thinking is that it is in the 3-5 cmH2O range. PEEP itself, however, does not expand alveolar segments. Mean airway pressure (PAW) is a time-average pressure accounting for both peak inspiratory pressure (PIP) and PEEP. As long as PAW exceeds critical opening pressures and there is positive airflow, recruitment will occur. PAW can be calculated as follows: (PIP×inspiratory units [time]+PEEP×expiratory units [time])/total number of units=PAW). (As an example for I:E at 1:2 PEEP at 5, PIP at 20: (20+5+5)/3=10 and I:E 4:1 PIP 20 PEEP 5: (20×4+5)/5=17). Recruitment is achieved by peak and mean airway pressures which exceed the critical opening pressures of collapsed alveoli. PEEP is important for maintaining recruitment.

Gas Flow in Brief.

In a lung, air flows from regions of higher pressure to regions of lower pressure at rates which can be predicted based on the pressures, volumes, tube diameters, reservoir capacities and measures of distensibility and elasticity, as well as the types of flows involved. Laminar flow is smooth and unidirectional, whereas turbulent flow, which often occurs as gasses bounce off boundary layers, involves many more local variances in flow and is less efficient. This can be expressed by the Reynold's number, where Re<2000=Laminar Flow, Re 2000-4000=transitional, Re>4000=turbulence. In general, lower flow rates have a lower Reynolds number and reduce the turbulence of flow.

When air flows at higher velocities, especially through an airway with irregular walls, flow is turbulent, and tends to form eddies. This is found mainly in the largest airways, like the trachea.

It is expected that flow though smooth airway tubes will be mostly laminar with some possible turbulence at the ends of the tubes as gas is forced into a larger area of relatively lower pressure. Further, gas under pressure will push through small diameter airway tubes more readily than the lungs into which they are inserted. Large amounts of air can flow through relative choke points. While in a lung, the air flow can remain continual and at a predictable and even rate. The common thinking of flow per minute is erroneous, as breaths take less than a minute and flow is not evenly distributed over long timespans in traditional ventilatory modes. Thus, failure to think in flow/sec can blind ventilator operators and designers to points which the current invention attempts to utilizes. In a clinical setting, obtaining a continuous low-flow/sec state is critical to avoid regional overdistension and achieve a homogeneous gas distribution.

Acute Respiratory Distress Syndrome (ARDS)—Pathological Basis, and attempts at mitigation Generally, ventilation problems can be defined as either outflow obstruction (such as in emphysema and asthma), or restrictive, where the lungs are hard to inflate (such as in fibrotic processes or cases of circumferential burns to the trunk which yield a tightening of the skin preventing chest wall excursion).

Three types of ventilator induced lung injury have been well documented:
1. barotrauma (injury from too much pressure),
2. volutrauma (injury owing to overstretching with too much volume per vent breath, which has been shown to cause inflammatory cytokine release), and
3. atelectrauma (sheer force injury from collapse and repeated re-expansion of the alveoli).

Safe "recruitment" is the re-expansion and maintenance of (non-injurious) inflation of alveolar units previously collapsed (atelectatic) by disease processes.

Two basic types of ventilation have historically been undertaken. The first, volume control, occurs when the user sets a volume which results in the generation of sufficient pressure to fill the lung. This can result in barotrauma if the lung is stiff. The second main category of ventilation is termed "pressure control." In pressure control modes, a driving pressure is set and, depending on the compliance of the lung, as measured, amount of air flows in as a result until the set pressure is reached. With stiff lungs, this can result in hypoventilation, hypercapnia and acidosis. When lungs that are improving, but with unmonitored compliance, such a mode can yield volutrauma.

ARDS is a well-documented syndrome with myriad contributing pathologic causes. Historically, ARDS is defined, whatever the cause(s) for a particular patient, by a poor partial pressure of oxygen in arterial blood ($PaO_2$) to fraction of inspired oxygen ($FiO_2$) ratio (P:F). This falls into the restrictive lung disease category. Typically, compliance is poor, and many lung regions are profoundly hypoventilated showing a "ground-glass" appearance on an x-ray. If such a patient is ventilated with normal volumes, and the lungs are stiff, $CO_2$ elimination is low and ventilator induced lung injury (VILI) in the forms of volutrauma, atelectrauma, and barotrauma can result.

In ARDS, it is known that a system of dynamic disequilibrium exists such that whatever lung segment is made dependent (down) will become the hardest to aerate.

In response to these problems, several responses have been tried.

Gattinoni (2005) proposed the idea of the "baby-lung." The concept is that the usable lung parenchymal volume is 300-500 ml, that of a 6-year-old child. Gattinoni proposed volume control and gentle ventilation to maintain the well aerated lung segment in such settings, noting that higher volumes may be injurious. Unfortunately, this idea of saving the baby-lung is unambitious and results in accepting loss of lung capacity for the patient. Instead, the goal of therapy should not be the maintenance of what remains in a disease state, but the eradication of the disease state.

Nevertheless, the idea of the baby-lung and the ARDSNet trial of 2000 have combined to create a pervasive mindset among ICU providers which advocates several ideas implemented concurrently.

First, high PEEP is used to maintain open segments. Since change in pressure yields tidal volume, the result of high PEEP is that, according to national clearinghouse practice guidelines, volumes must be limited to avoid barotrauma. For example, if a ΔP of 20 cm $H_2O$ is required for a volume of 600 ml, and the PEEP is set to 18, then the PIP would be 38 for that volume which is in the range known to cause trauma.

Secondly, since lung volume must be lower and $CO_2$ still needs to be eliminated, ventilatory rates must be increased. When inspiratory cycle time decreases, so do inspiratory phase durations assuming a physiologic I:E ratio. When inspiratory phases are shorter, flow increases and the result to an atelectatic lung is a regional overdistension. Gattinoni acquiesces and argues for permissive hypercapnia, which has the sequelae of acidosis, and is therefore also undesirable. Nor did Kallet, (R. 2018) find any increase in efficacy between low PEEP and recruitment maneuvers in a study of over 1,000 patients with ARDS.

Some practitioners, such as Dr. Nader Habashi, have opted instead for time-cycled pressure limited pressure driven modes of ventilation such as airway pressure release ventilation (APRV) with long inspiratory phases and no set PEEP. Additionally, expiratory durations are so short that very little volume can escape before the next breath, with the resultant residual volume providing PEEP. The hope is that this will cause a more homogenous gas distribution, better $CO_2$ elimination, less regional overdistension related volutrauma, less barotrauma, and more recruitment and less atelectrauma. These methods show promise, but have not solved these issues.

Other attempts have included high frequency oscillating ventilation (HFOV) and jet ventilation. The former uses tidal volumes so small that respiratory rates are measured in Hertz, but expiratory phases, are still required, and mean pressures remain high with natural flows discarded in favor of mechanisms which essentially "bounce" molecules along in the airway. "in the adult," (HFOV) "uses breathing frequencies of 180-900 breaths/min (3-15 Hz) with resulting small VT, often less than anatomic dead space" . . . "Similar to conventional ventilation, inspired oxygen can travel as a bulk flow and reach proximal alveoli. Longitudinal dispersion occurs by combined convective flow and diffusion." . . . "in subjects with moderate ARDS. There was no significant improvement in the $PaO_2/FIO_2$ at 12 h in the supine HFOV arm, whereas both the prone conventional ventilation and prone HFOV groups showed a significant improvement" (Nguyen et al, 2016). A significant limitation of the mode is that, "requires synchrony with any existing patient breathing efforts. Spontaneous respiration results in a reduced airway pressure that the ventilator may interpret as a circuit disconnect, subsequently stopping ventilation." (Papazian et al, 2005). This feature makes ventilator wean hard and often requires significant sedation and paralytic drugs. Therefore, while HFOV offers theoretical benefits it is not a panacea at the level of daily clinical praxis.

Jet ventilation, is another manifestation of sequential tidal ventilation (breathe in: breathe out). This is typically accomplished through a 14-gauge (ga) catheter, outer diameter (OD) 2.1 mm, internal diameter (ID)~2 mm, allows flow rates of approx. 250 ml/min, and though, through the use of high inspiratory pressures hypercapnia and resultant acidosis can be avoided readily for periods of 15 min at least, though at a pressure of 45 psi (Ward et al, 1991). However, in a 50-600 min experiment on 25 kg pigs showed that with jet ventilation, "Oxygenation and ventilation were acceptable for 4 mm ID or more, but hypercapnia occurred with the 2 mm stent" (Slitterlin et al, 2015). Indeed, the current use of this invasive technology is such that it's hard to find examples in literature in the past 20 years with durations of adult human ventilation beyond those required for procedures such as intubation in the setting of airway obstruction and ventilation during bronchoscopy. Neither procedure typically exceeds 15 min in duration. Therefore, though it bears a superficial resemblance to a single element of the disclosed invention, in that narrow tubing is used, jet ventilation can't be considered a serious long-term plan for mechanical ventilation in the ICU setting.

However, even with APRV, a limiting factor exists to recruitment, that is, the need to exhale. Humans have a single lumen trachea and rely on tidal flow, so air must escape the way it comes in or the person must retain $CO_2$ and eventually die of acidosis. Only extracorporeal membranous oxygenation (ECMO) allows for $CO_2$ removal without an expiratory phase as this is effectively heart-lung bypass, and cardiopulmonary bypass, which results in mechanical destruction of red blood cells as they are circulated outside the patient. ECMO use is associated with a high mortality rate and considered a last-ditch therapy. If a mode of ventilation could be found which allowed for continuous recruitment and $CO_2$ elimination to normal levels, it would theoretically surpass the utility of most existing modes in the setting of restrictive lung diseases among intubated patients.

As conceived, the disclosed invention will be used in both the ICU and surgical settings where ventilating a patient is needed. Importantly, a ventilator mode which allows the lungs to remain still is very valuable in a thoracic surgery. Surgeons can work more freely and safely while also allowing an early warning if sedation wanes, since the patient's diaphragm will move before peripheral nerve stimulation. This reveals that sedation is wearing off. Therefore, the thoracic surgery setting is an important application space for the dual lumen, continuous flow airway design.

A ventilator system which allows for continuous inspiration and intermittent—concurrent expiration, such that the lungs are kept at near maximum safe inflation and $CO_2$ is eliminated to normal levels, would make continuous recruitment possible. Such a system needs to have separate inflow and outflow tubes which will divide the native airway for this purpose. The system, owing to an effectively nearly infinite inspiratory phase, can be a low-flow system and thus be lung-protective and pro-recruitment in the setting of, or for the prevention of, ARDS. Since there will always be air within the lung it is unlikely that additional PEEP will be required, mean pressures will approach PIPs thus overcoming critical opening pressures, and pressure readings will be displayed on the ventilator. Homogenous gas distribution will allow optimal $CO_2$ elimination per unit volume.

Further optimizations include flow titration based on real time feedback from expired $CO_2$ sensors, possibly also featuring a capnographic waveform display, inline, and a pressure limiting valve trigger for expiration in the event that only low pressures are needed for ventilation. Thus, when a set pressure was reached due to air buildup, allowing the expiratory tube to open within the ventilator, and air would flow out until a lower set pressure was reached and noted by onboard systems. In the setting of less compliant lungs requiring higher pressures, the threshold, set by the operator, could be low, allowing for the valve to remain open continuously and simultaneous inspiration and expiration with flow sufficient to fully aerate would occur, but barotrauma would be nearly impossible to inflict.

Since there would be easy outflow of air, both apneic and spontaneously breathing patients could be placed in this mode with the expectation that patents could imitate additional expiration from diaphragmatic contraction at any point and would therefore not have to "fight the vent" as has been a problem in some modes wherein the breaths are timed.

Macro-Static Ventilation

The counterintuitive nature of a ventilation model without tidal breaths in apneic humans should be addressed. Since the airflow is continuous the flow rates are very low relative to what is found in normal spontaneous ventilation, this combines with concurrent venting for outflow to yield the gross appearance that the lungs do not move. $CO_2$ in this model is offloaded though convective flow, it is helpful to think of a convection oven and the unidirectional air flow through a grasshopper. Here instead of a cephalad to caudal route for such flow, as in a grasshopper, it is an inspiratory to expiratory tube flow pattern with the middle of that pattern, the convection oven, being the lungs. Another image that helps normalize this maco-static ventilation mode is that of analogy with a continuous-flow total artificial heart (CFTAH). With a CFTAH in place blood flow is not pulsatile, so the patient lacks a heartbeat, yet cardiac output, or flow per minute, is maintained in normal ranges. Gas flow through the lungs will be similar in apneic patients though additional tidal flow variation superimposed on the continuous flow mode by a spontaneously breathing patient is not prohibited.

Proof of Concept Porcine Lung Experiment

A new experimental round was undertaken following experiments performed in 2018 which were plagued by air leaks. On July 2019 a single set of ex-vivo porcine lungs approx. 10 hrs. postmortem (preserved on ice in a standard cooler for approx. 8 hrs. prior to use) were passively ventilated, but not perfused, on each of two systems. The voids within the proximal end of the ET tube were filled with pipe cleaners, circumferential compression clamps were applied external to the ET Tube wall, and the end of the ET Tube caulked with a silicone sealant to minimize leakage. The lungs did have a small (less than 2 cm) laceration on the posterior surface of the right lower lobe (RLL) and a Vaseline-gauze was applied thereto. There were also pre-experimental areas on the medial aspect of the left lower lobe (LLL) which resembled blebs, but which did not expand significantly with ventilation.

A tie was placed around the airway superior (cephalad) to the inflated ET tube balloon as the airway was quite large and leakage around the tube had to be controlled for. At no point was the liter flow per min >8, and no flow >5 L/min was used for any purpose other than initial recruitment from a flaccid and deflated baseline. Neither a bag valve mask nor any PEEP valve was ever employed. Between the $O_2$ tank and the inspiratory tube was a standard 7 ft oxygen tube, and another similar tube was attached to the expiratory tube and then in sequence, to a pressure gauge and a hand-held flow meter. No sealant was used at these joints. 8.5 mm ID ET Tubes were used to accommodate the dual lumen model. Videos and still images were obtained to document the experimental picture and readings on the above devices.

Build 1: Inspiratory and Expiratory tubes of the same diameter: 4.318 mm ID
Recruited with 8 L/min max flow
Resting state: 5 L/min Flow in
Measured Exp Flow: 4-4.5 L/min
Exp Tube Pressure: 27.5 cm H2O
Build 2: Inspiratory Tube 2.3815 mm ID, Expiratory tube 4.318 mm ID
Recruited with 5 L/min max flow
Resting state: 4 L/min Flow in
Measured Exp Flow: 3-4 L/min
Exp Tube Pressure: 22.1 cm H2O As this was a non-perfused model, products of metabolism, respiration, and the clearance of $CO_2$ as would normally be shown by arterial blood gas or end tidal carbon dioxide ($ETCO_2$) were unavailable.

Findings and Conclusions

Since a normal respiratory rate in adults is 12-20 breaths per minute, traditional physiologic vent settings might include a rate as low as 12/min (cycle time 5 sec) with a volume of 500 ml/vent breath being a common volume for patients who are not exceedingly tall. At a 1:2 I:E ratio this would equate to an inspiratory flow rate of 312.5 ml/sec. With build 1 in the macro static model, so named as the lungs appear motionless to the untrained eye during continuous ventilation with convective flow, even when using a recruitment flow of 8 L/min, the flow was 133 ml/sec since 8,000 ml are delivered evenly over 60 seconds (8,000/60=133.3). Once recruitment was achieved, the flow was dropped to a flow of 5 L/min or 83.3 ml/sec. In build 2 the flow rate of 4 L/min was 66.6 ml/sec. These much lower flow rates should promote optimized $CO_2$ clearance vs. tradition physiologic I:E tidal ventilation. The low flow rates:

1. avoid regional overdistension of function lung units
2. promote homogeneity of gas distribution, per APRV practice
3. provide expiratory pressures in the known safe range
4. provide gentle and continuous recruitment of the lung In order to be placed on a ventilator, a patient is intubated. This means having an endotracheal tube placed in the mouth (or nose) and threaded down into the airway as shown in FIG. 3. The endotracheal tube has a small inflatable cuff which is inflated to hold the tube in place and to seal off any outflow of air around the tube. Thus, the inner lumen of the tube becomes the only path for airflow in and out of the lungs. A ventilator is attached to the tube and ventilates the patient.

When a patient is on a ventilator, medication is often given to sedate the patient. The reason for this is because it can be upsetting and disturbing to the patient to have an endotracheal tube in place and feel the ventilator pushing air into the lungs.

Weaning is the process of removing a patient from the ventilator. Most surgery patients are removed from the ventilator quickly and easily. A nasal oxygen supply (or mask) often makes the process easier.

Depending on a given patient's pathology and care plan he or she may be quickly removed from mechanical ventilation, while others patients with differing pathology and treatment needs will require a longer weaning process. In the latter case the ventilator is adjusted to slowly wean the patient from the ventilator. This may take days or even weeks, gradually allowing the patient to improve their breathing.

A typical ventilator has several modes of operation. CPAP mode, or continuous positive airway pressure, is a ventilator setting in which the patient initiates the breath, but then the ventilator helps by pushing more air in than the patient would draw in by themselves. This makes each breath easier than it would be without ventilator support. Other modes are utilized as already mentioned.

Some patients who are on the ventilator for an extended period of time may be on CPAP during the day, will full ventilator support at night so they can fully rest and continue to heal without being exhausted by the work of breathing.

Based on examples in nature, a mode of ventilation that features simultaneous inspiration and expiration is achieved by offering concurrent inspiration and expiration using periodic expiratory valve triggers. The triggers include $ETCO_2$ levels and peak inspiratory pressure (PIP) thresholds. When coupled with an innovative supplemental dual lumen airway, using the native endotracheal tube, continuous inspiration and exhalation is possible without the need to "breathe in and out" separately. This provides a gentle, safe, and continuous ventilation by keeping the lungs open and well aerated, and avoids hypercapnia and resultant acidosis as well as atelectasis.

The term inspiratory air, or air flow, means air or other gas mixtures that is enriched by oxygen that is given to a patient in ventilator situations, and may be additionally enriched by other additives such as medication. Similarly, the term expiratory air or air flow, means the inspiratory air after it leaves a patient's lungs. General use of the term air or air flow means the gas may be atmospheric, inspiratory, or expiratory air, depending upon the context. The use of the word lumen is common in the art, and refers to an airflow passageway, usually inside a flexible tube, most often round. The use of the word tube in this application means a physical tube, and includes the airway (or lumen) through it. The use of inspiratory line and expiratory line means a connectable inspiratory tube and connectable expiratory tube respectively.

FIG. 1 shows a simplified drawing of an endotracheal tube assembly, a left and right lung 104a,b, and lung bronchus 105. The inspiratory tube (or lumen) 102a sends airflow into an inspiratory airway channel (or lumen) 102b which flows down to where the primary (left and right) bronchus airways separate. Air flows out of the inspirator tube and into the lungs in continuous fashion, with modulated pressure changes. The air flows into the rest of the bronchus 105 airways and into the lung alveoli 106 as this represents the path of least resistance to gas flow. The inner expiratory tube (or lumen) 103 receives the expiratory airflow based being a low pressure relative to the lungs when the expiratory valve is open and is further controlled/monitored as illustrated in FIG. 4B. An inflatable cuff 101 seals off the airflow around the endotracheal tube to prevent air leaks. FIG. 3 better illustrates the endotracheal tube.

The left primary bronchus and right primary bronchus join at the tracheal carina 112. The expiratory tube 103 end is located at a distance 111 of 2-4 cm superior to and in a cranial direction from the tracheal carina. The expiratory tube 103 extends 110 about 2 cm beyond the end of inspiratory airway channel 102b (or 4-6 cm superior to the tracheal carina). The inspiratory airway channel is the length and volume of the endotracheal tube that is not occupied by any other tube. These positions are important for creating a well ventilating lung.

Figure 2A:
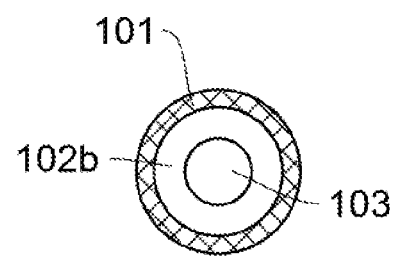
FIGS. 2A-2B show cross sections of the endotracheal tube in two locations.
Figure 2B:
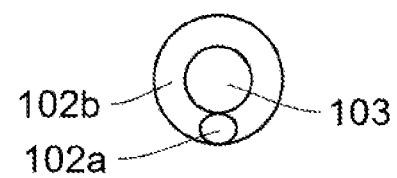

FIGS. 2A-2B show cross sections of FIG. 1 endotracheal tube. A cuff 101 is filled with air to seal the air flow around the endotracheal tube, and prevent gas from leaking around it. Cuffs are well known in the art of endotracheal tubes. An approximate position for the expiratory tube 103 and inspiratory airway channel 102b is shown. The inspiratory airway channel 102b is the area around the expiratory tube. In FIG. 2B, the inspiratory tube 102a is shown, which feeds inspiratory flow into the inspiratory airway channel.

Figure 3A:
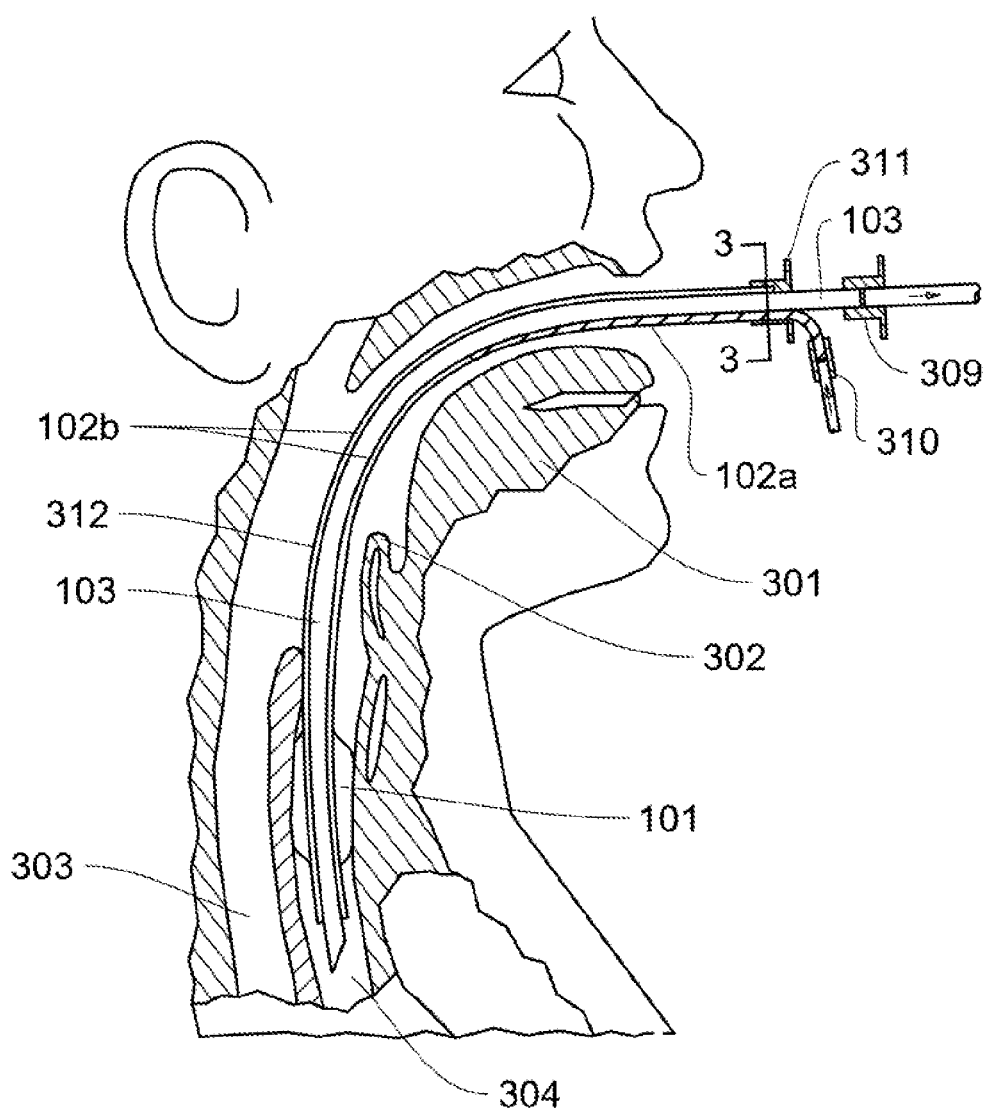
FIG. 3A shows a preferred ventilating tube arrangement in the airway of a patient.

FIG. 3A shows the inspiratory/expiratory tubes of FIG. 1A-1B which are located in the patient's endotracheal tube which is placed in the patient's airway. The Tongue 301, Epiglottis 302, trachea 304, and Esophagus 303 are labeled for anatomical orientation. The inspiratory tube 102a is located inside the inspiratory airway channel 102b and conveys inspiratory airflow into the inspiratory airway channel. An inspiratory tube connector 310 connects the inspiratory tube, and a separate connector 309 connects the expiratory tube 103. The inspiratory tube is connected to the inspiratory airway channel by use of an end connector 311 which seals the end of the inspiratory airway channel. The inflatable cuff 101 is shown. The view at line 3-3 is shown in FIGS. 3B-3E for a variety of inspiration/expiration tube arrangements.

The outer endotracheal tube (or airway tube) 312 for the inspiratory airway channel 102b must already be in place when the patient is connected to a ventilator that operates according to the methods of the embodied invention. The outer tube could be a single lumen (endotracheal) airway that is used for other types of common ventilators such as used in emergency response operations. In this case, the inner expiratory tube 103 along with the inspiratory tube are inserted into the single lumen tube and the flows to and from the patient are connected to the embodied invention.

Tube markings are used for positioning the expiratory tube inside the endotracheal tube. This allows the clinical staff the ability to correctly position the tubes where they are the most effective. An endotracheal tube cuff 101 is inflated when the endotracheal tube is positioned. The cuff is normally inflated by a pressurizing syringe and connecting tube (not shown).

Alternately, a tracheostomy tube from a surgical tracheostomy procedure could equally be used for ventilating a patient if medically needed. It would have the same operative control as an endotracheal tube.

Figure 3B:
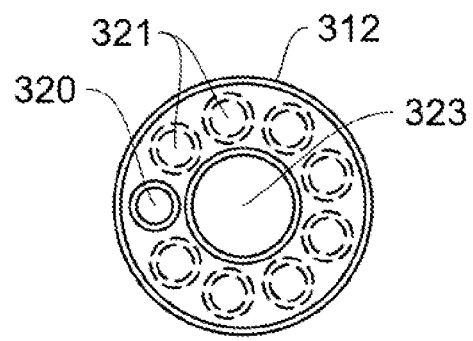
FIGS. 3B-3H show exemplary inspiratory and expiratory tube arrangements and connectors.

FIGS. 3B-3E are examples of routing the inspiratory and expiratory flows through the outer endotracheal tube 312 at line 3-3. In FIG. 3B, the inspiratory tube 320 and the expiratory tube 323 are shown. An additional array of inspiratory tubes 321 are optionally added. The number of added inspiratory tubes is flexible.

Figure 3C:
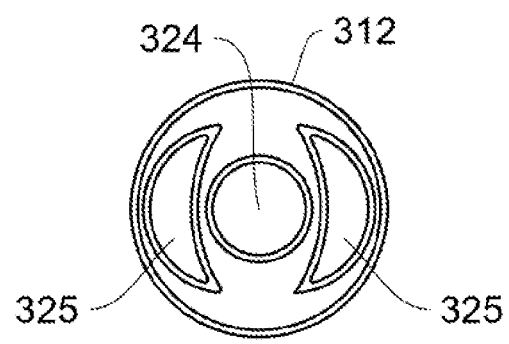
Figure 3D:
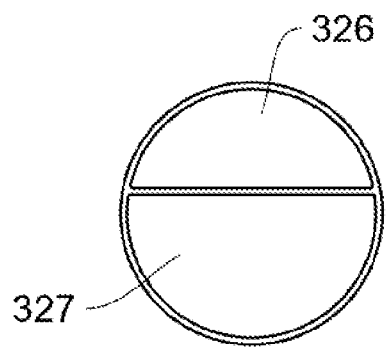
Figure 3E:
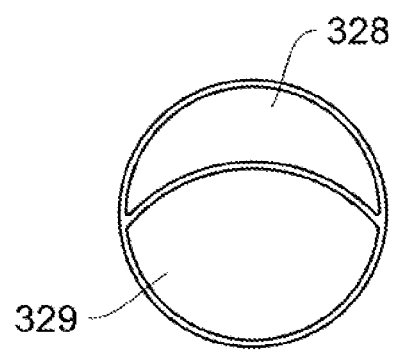

In FIG. 3C, an alternate expiratory tube 324 is shown with a pair of partial circle shapes 325 for the inspiratory tubes. In FIG. 3D, the inspiratory 326/expiratory 327 tube shape is a split circle for a 40-60% ratio. Similarly, in FIG. 3E, the inspiratory 328/expiratory 329 shape is a modified split circle.

Figure 3F:
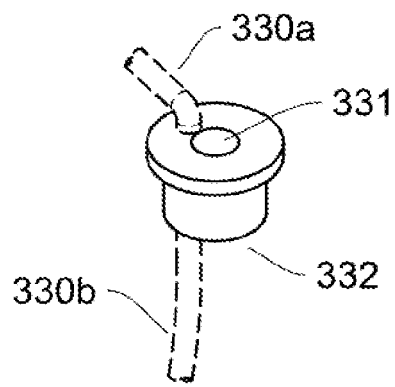
Figure 3G:
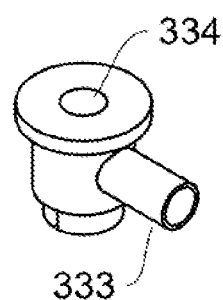
Figure 3H:
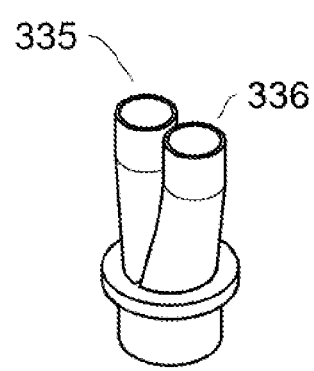

FIGS. 3F-3H are exemplary end connectors for the inspiratory/expiratory airway shapes through the endotracheal tube. FIG. 3F is a connector as shown in FIG. 3A. An inspiratory tube 330a, 330b passes through the connector 332 which caps and seals the end of the endotracheal tube. An expiratory tube hole 331 allows the expiratory tube to pass through the connector.

FIG. 3G is an alternate connector with a side inspiratory connector 333 and also has an expiratory tube hole 334. This connector is adaptable for the expiratory—inspiratory tube shapes such as shown in FIG. 3C.

FIG. 3H is an alternate connector with two connections 335,336 for the inspiratory and the expiratory lines. This connector is adaptable for the expiratory inspiratory shapes as shown in FIGS. 3D and 3E.

The exemplary inspiratory/expiratory tube shapes shown in FIGS. 3B-3E are examples, and other connectors are possible. Sealing methods when connecting tubes to prevent leakage is done by methods known in the art of tubing connectors.

Figure 3I:
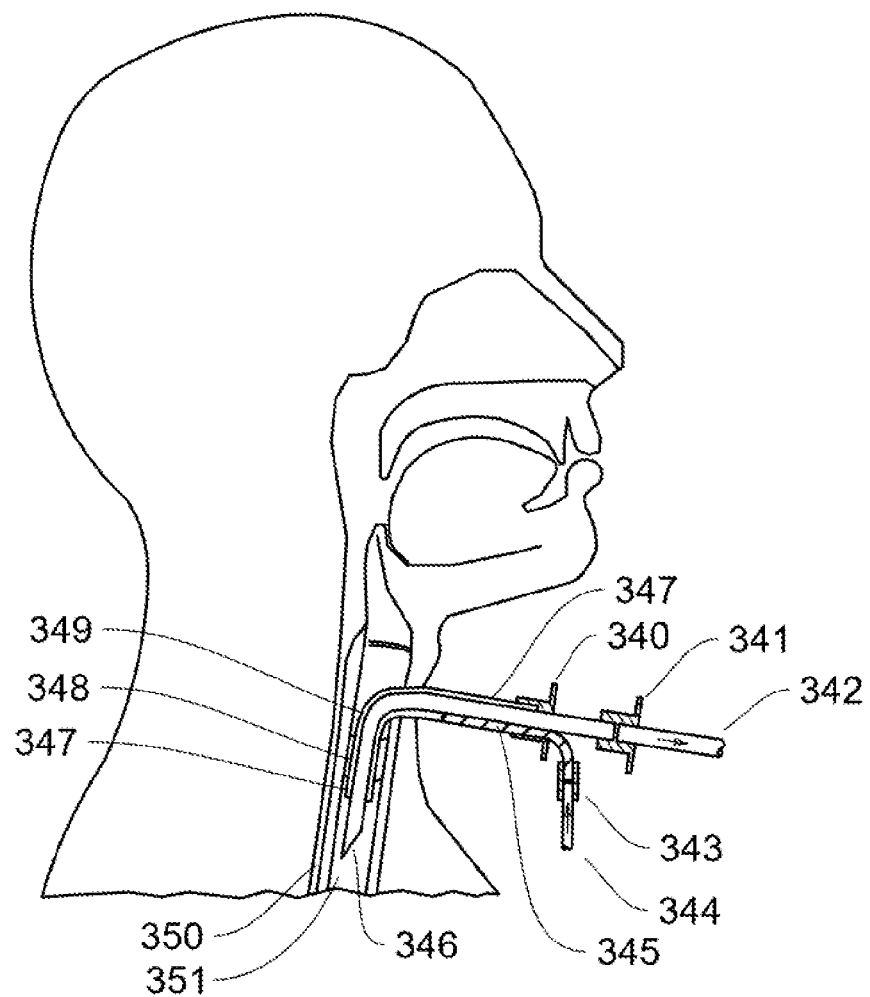
FIG. 3I shows an embodied use of a tracheostomy tube.

FIG. 3I shows an alternate embodiment where a tracheostomy tube from a tracheostomy procedure is adapted for ventilation control according to the disclosed invention. Similar to FIG. 3A, an expiratory tube 346 is placed inside a tracheostomy tube 347 (or airway tube) previously installed during a surgical procedure. A cuff 348 is used to seal the patient's trachea. The expiratory tube 346 is connected to an expiratory line 342 using a connector 341. An inspiratory line 344 is connected to an inspiratory feed 345 by an inspiratory connector 343. The inspiratory connector 340 seals the end of the tracheostomy tube 347, and directs the inspiratory flow into the airway 349 between the tracheostomy tube 347 and the expiratory tube 346. The trachea 351 and esophagus 350 are labeled for anatomical orientation.

Figure 4A:
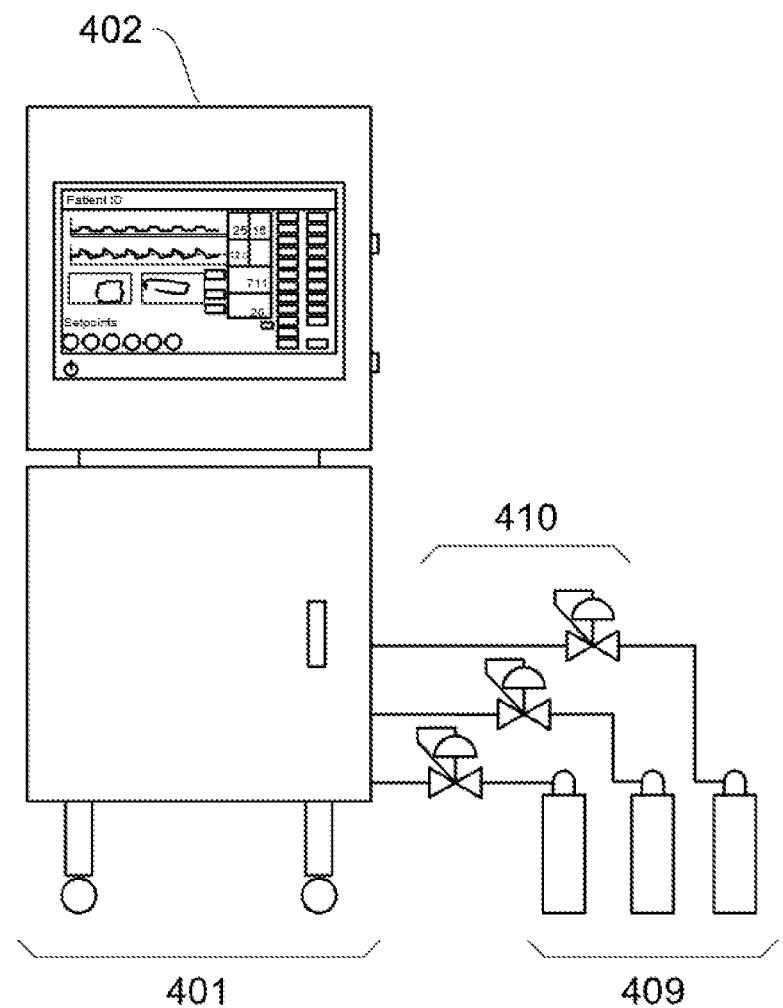
FIG. 4A-4B show the equipment used to control ventilation in the patent along with an XY sensor.
Figure 4B:
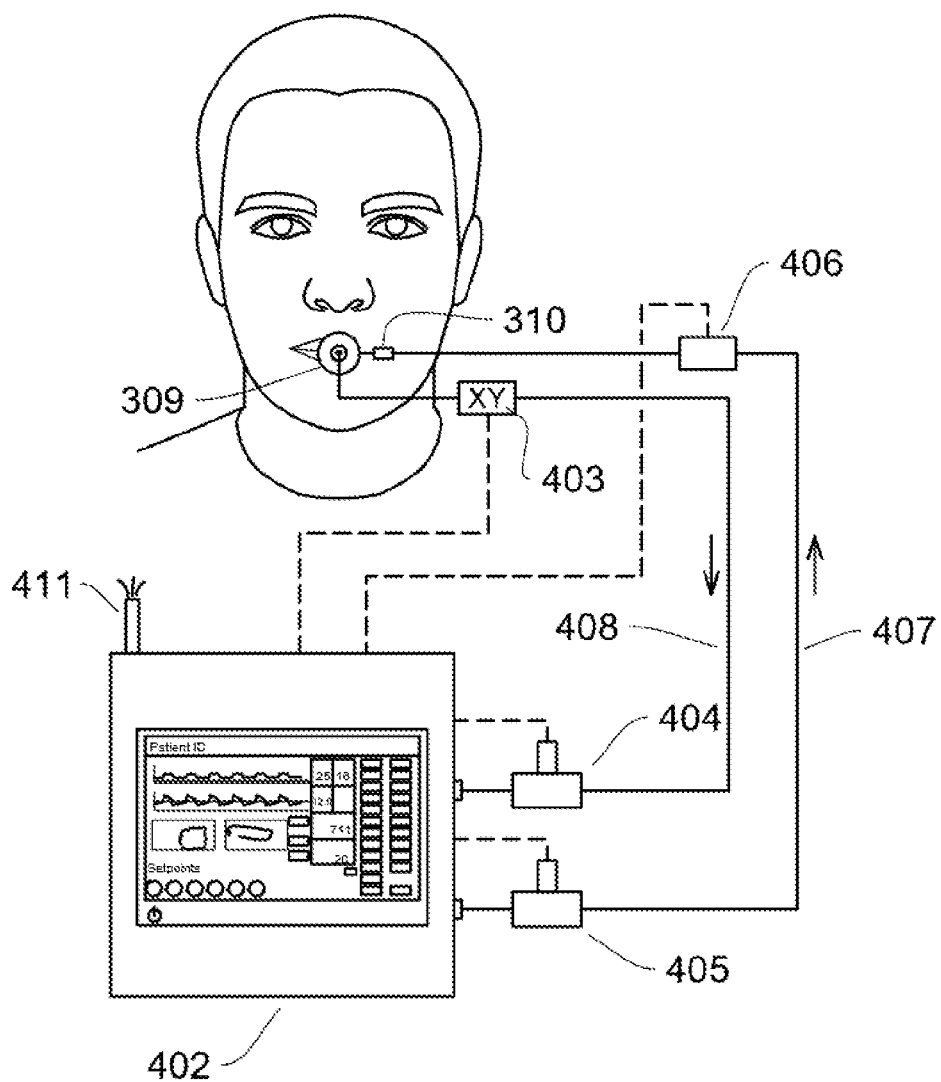

In FIG. 4A, a typical control station is a mobile cart 401 with all the controls needed to regulate the oxygen and breathing pattern for the patient. Typically, the cart plugs in to the hospital power, and will control independently. It also has a battery for mobile use for at least two hours.

The air/oxygen/medication supply typically has two or more gas modules, one for air and one for $O_2$. Gases are supplied by a medical pipeline system, a compressor, or by gas tanks 409 (illustrated) with a pressure regulating valve 410. Internal to the mobile cart, the oxygen containing gas for the patient is mixed to specific ratios to supply the correct oxygen amount per breath. Other gases may be mixed in such as nitric oxide (NO) to stent open alveoli and prevent atelectasis.

FIG. 4B shows a generalization of the airway system used for inspiration flow and pressure, as well as monitoring the expiration flow. A control panel 402, with associated computerized controls, monitors the pressure and flows going into the patient. An inspiration flow rate is monitored by an XY flow sensor 403. The XY sensor provides a combination lung pressure reading X and an air flow reading Y to the microprocessor control unit (MCU) in the control panel. The inspiration air flow is optionally humidified (not shown) for the patient's comfort. An inspiratory flow rate sensor 406 monitors the inspiratory air flow to the patient. The inspiratory line 407 is connected to inspiratory tube connector 310 near the patient's mouth, which is routed through the internal inspiratory tube inside the patent. An expiratory connector 309 connects to the expiratory flow line 408.

Two control valves, an inspiratory valve 405 and an expiratory valve 404, are controlled by the MCU inside the control panel. Inside the control panel is an oxygen sensor and a $CO_2$ sensor (not shown) that monitors the expiratory flow. The expiratory air vents 411 from the control panel. Alternately, the $CO_2$ sensor is integrated into a small device that connects directly at the airway, between the breathing circuit and endotracheal tube.

Figure 5:
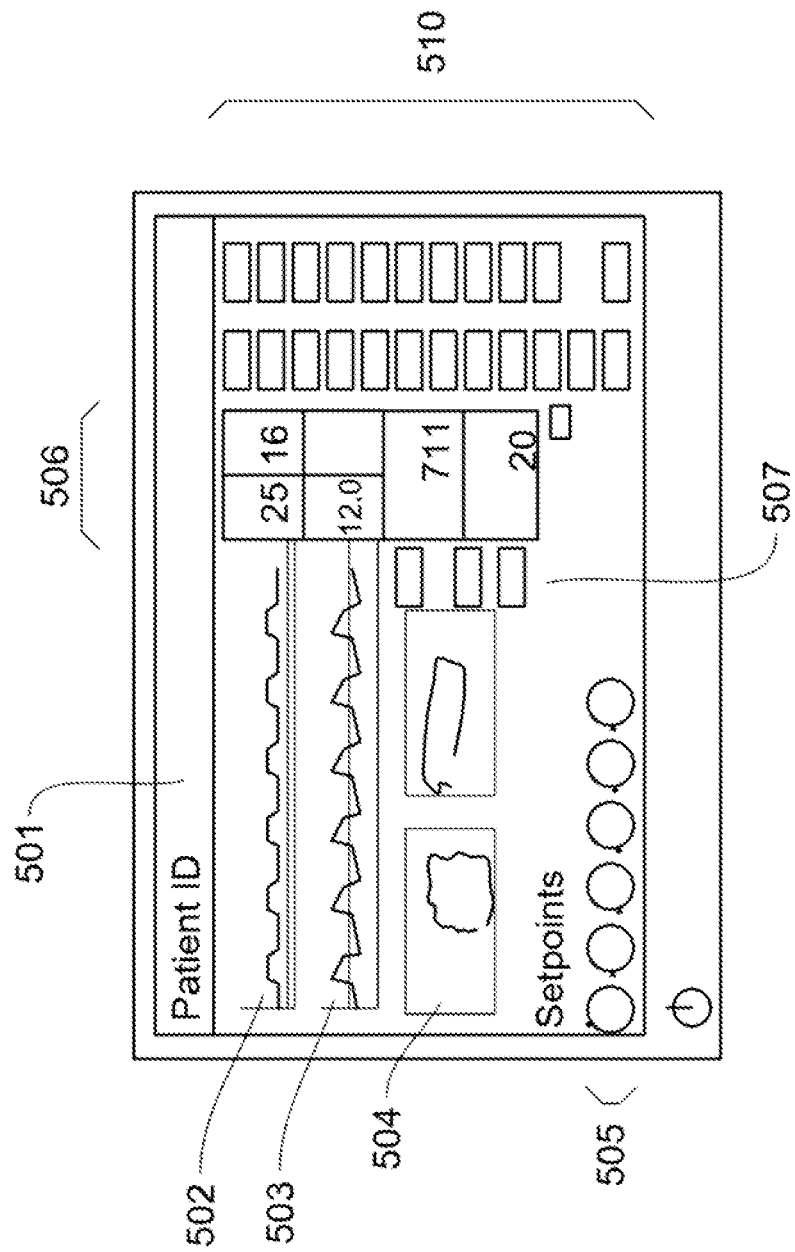
FIG. 5 shows a typical display and control interface for the new biomimetic flow based pressure limited ventilation mode.

As seen in FIG. 5, a typical ventilator operator interface display for a patient is shown. The interface includes:
1. A patient ID banner at the top 501
2. Lung pressure graph 502 with instant reading of current value to right.
3. Lung flow graph 503 with instant reading of current value to right.
4. Lung volume tracing charts 504
5. Setpoints for lung control and alarm values 505
6. Various instantaneous readings 506

7. Panel touch-screen control bars for reading units 507
8. Computer touch-screen control bars to switch to new displays for alarms, various control pages, information pages, setup pages, etc. 510

The computer control is preferably a microprocessor control unit MCU capable of monitoring all the sensor data, interfacing with the touch display, retaining setpoints, performing control loop and monitoring functions, creating alarms, providing external wireless or wired communication with remote sensors, data storage memory, includes an operating program, and communicates with other computers. The MCU has volatile and non-volatile memory to retain operating information and setpoints, and has needed processing speed and capability to communicate with displays and operator input. The microcontroller contains one or more CPUs (computer processor cores) along programmable input/output for peripheral sensors and displays. Preferably program memory in the form of ferroelectric RAM, NOR flash, or OTP ROM, as well as random access memory RAM.

Generally, display items on the display screen in FIG. 5 are known in the art of ventilators, and anesthesia machines, unless noted.

Preferably, the operator interface screen utilizes both touch sensitivity and a scroll button and allows "clicking" on highlighted items (or combination of the above.) These are the current industry standard and well known in the art.

In FIGS. 6A-6D show charts for lung pressure, expiratory lung flow rate, and inspiratory flow rate according to the conceived invention when a patient is not breathing on their own. The x-axis for all the charts is time. The lung pressure is in the upper graph and the pressure is measured in centimeters of water. The middle graph is expiratory flow rate in ml/sec and the lower graph is the inspiratory flow rate in ml/sec. Flow rates are optionally shown in Liters/min.

Pressure triggered, pressure limited, flow based control mode.

In FIG. 6A, an embodied flow pattern into and out of the lung is shown when a patient is not breathing on their own, and a lung pressure cycle is regulated by a ventilator. When using this ventilator control, the lung pressure is maintained between a minimum pressure 601 setpoint and a maximum pressure setpoint 603. The inspiratory flow rate is held at a constant 605 setpoint and at an amount that will inflate the lung over time. Additionally, the flow rate is dependent upon a number factors that are discussed in section 'preferred setpoints'. When there is a minimum inspiratory flow rate, and a zero expiratory flow rate, the lung pressure will rise as shown the upper graph.

a) At time 602, when the lung pressure reaches the high pressure setpoint 601, an expiratory flow is triggered, and causes the expiratory control valve to open. The lung pressure then peaks slightly above the high pressure setpoint, and then declines. The expiratory flow rises to a peak and then declines back to zero. The inspiratory flow is held constant at the inspiratory normal flow setpoint 605.

b) At time 604, the lung pressure has lowered to the minimum setpoint level 601 and this causes the ventilator control to close the expiratory flow valve. The inspiratory flow is held constant at the inspiratory normal flow setpoint 605. The lung pressure then rises. Since the lung is maintained at a minimum pressure, the lung does not significantly inflate or deflate during the control cycle.

c) At times 606 and 608, the same control is repeated.

The control continues to repeat and provides both ventilating air and pressure recruitment of the lung until the operator changes the control or disconnects the patient from the ventilator.

Spontaneous breath control modification.

Figure 6B:
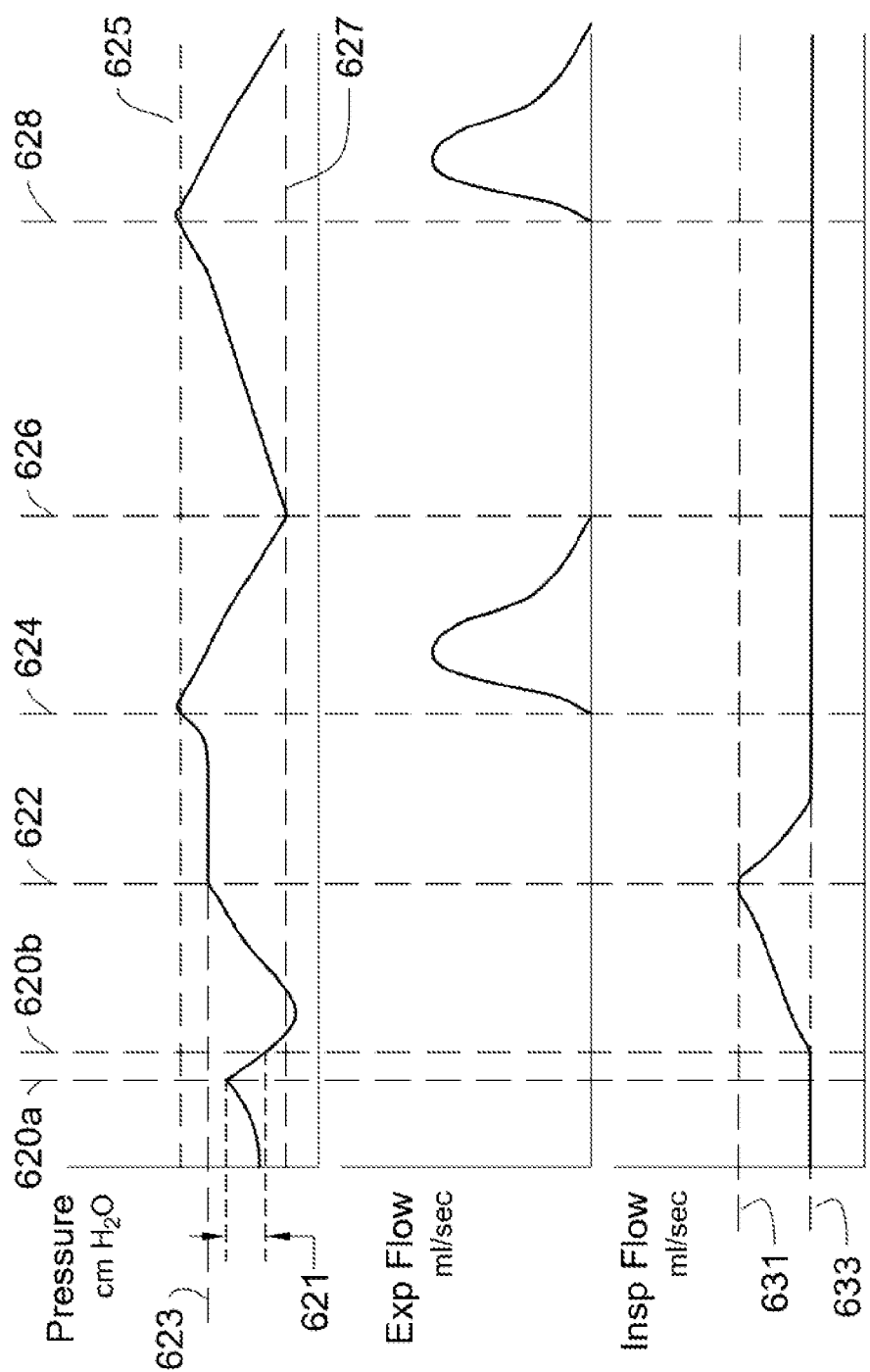

FIG. 6B shows ventilator lung pressure and flow control when the patient initiates a spontaneous breath cycle by moving their diaphragm. The movement may be initiated consciously or unconsciously.

a) For the time between 620a and 620b, a spontaneous breath desire occurs—the lung pressure drops due to a patient diaphragmatic contraction within a short time.

b) At time 620b, the lung pressure drop 621 is high enough (about 2 cm $H_2O$ less than 3 seconds) for the controller to recognize a 'spontaneous breath' while the expiratory control valve is closed. The pressure drop causes the inspiration flow rate to increase to the high inspiration flow setpoint 631. The lung pressure rises due to increased inspiration flow. The expiration control valve is still closed.

c) At time 622, the lung pressure rises to a 'spontaneous breath complete' high pressure setpoint 623. This causes the inspiration flow rate to be reduced to a normal flow setpoint 633. The lung pressure plateaus as the lung enlarges and then the pressure increases.

d) At time 624, the lung pressure reaches a high pressure setpoint 625. This causes the expiration control valve to open and the expiration flow rises and falls. The lung pressure drops. The inspiration flow continues at a constant flow rate.

e) At time 626, the low lung pressure setpoint 627 is reached, causing the expiration valve to close. The inspiration flow continues at the normal flow setpoint. The lung pressure rises again due to inspiration flow without expiration flow. In this case, no additional 'spontaneous breath' occurs.

f) At time 628, the lung pressure rises to the high pressure setpoint 625. This causes the expiration valve to open and the lung pressure falls.

Typically, control continues utilizing the pressure triggered, pressure limited, flow based control previously described if no additional spontaneous breaths occur.

De-Recruiting Control Modification.

In FIG. 6C, the lung pressure and flows are shown for a patient during a de-recruiting event. That is, the lung pressure is unregulated for a short time, and the lung is allowed to significantly deflate. Typical situations for this include:

a) When a patient is moved from one hospital unit to another and needs to be switched to from a portable ventilator to a stationary ventilator.

b) When a patient is brought in by an emergency response team, and the patient needs to be switched from a portable 'bag type' ventilator to a hospital ventilator. In this case, the patient will also be intubated.

c) During surgery when collapsed lungs allows better surgical access.

d) When a camera is deployed into the airway of a patient.

e) For a lung treatment, such as flushing by sterile salt water (saline) or with instillation of other liquid medicines.

f) For deploying suction equipment into the patient's airway.

For the de-recruiting event such as moving the patient, the lung vitals are shown in FIG. 6C. The patient that is briefly disconnected from a previous ventilator control and re-connected to a ventilator control according to an embodiment of the invention.

a) Between times 640 and 642, when reconnecting the patient and turning on the ventilator, the lung pressure falls, and the expiratory flow drops toward zero as the patient exhales their reserve of air while there is no connected ventilator circuit. The pressure and expiratory flow are shown in dot dash lines.
b) At time 642, the patient is connected to the ventilator and the operator presses a start button to activate the control setpoints—low pressure 641, high pressure 643, inspiratory low flow 645 and inspiratory high flow 647. At this time, the lung pressure is below the low pressure setpoint 641, and this causes the expiratory valve to close. This also causes the inspiratory valve to open and move to the high flow rate control setpoint 647. The lung fills quickly and the pressure quickly ramps up due to the high amount of flow into the lung.
c) At time 644, the lung pressure reaches the high lung pressure setpoint 643. This causes the inspiratory flow to ramp down to the normal flow rate 645 setpoint. It also causes the expiratory valve to open. The expiratory flow rises and falls.
d) At time 646, the lung pressure reaches the low pressure setpoint 641 and this causes the expiratory valve to close. The constant inspiratory flow continues. The lung pressure rises.
e) At time 648, the lung pressure reaches the high pressure setpoint 643. This causes the expiratory valve to open.

Typically, control continues utilizing the pressure triggered, pressure limited, flow based control previously described.

Preferably, the high inspiratory flow rate 647 in FIG. 6C is the same as the high inspiratory flow rate setpoint 631 in FIG. 6B, but it is not a requirement. Similarly, the low inspiratory flow rate 645 in FIG. 6C is the same as the low inspiratory flow rate setpoint 633 in FIG. 6B, but it is not a requirement.

$ETCO_2$ Control Modification.

Figure 6D:
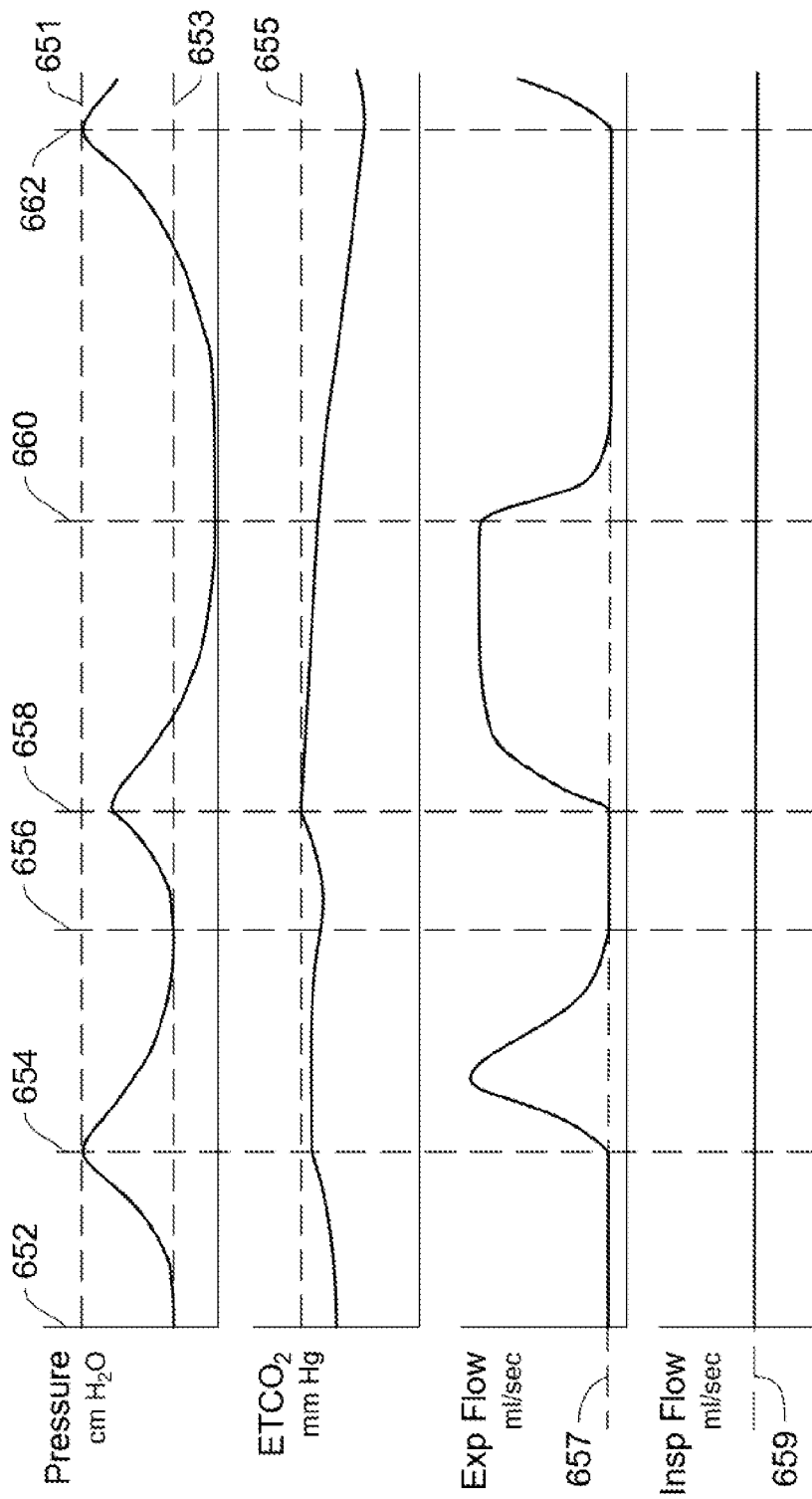

FIG. 6D shows a control using $ETCO_2$ as an expiratory control option in addition to the pressure triggered, pressure limited, flow based control. Over time, the amount of $CO_2$ may build up in a patient if there is insufficient expiratory volume over time. The $CO_2$ builds up in the body and needs to be 'offloaded.' Importantly, an $ETCO_2$ measurement is only possible during expiratory flow, as the $CO_2$ sensor is located in the expiratory line. To this end, a small amount of expiratory flow is added to the control based on an expiratory flow setpoint 657.

In this case, a high $ETCO_2$ setpoint 655 is added to the control. When the setpoint is reached, the expiratory valve, which is slightly open to allow $ETCO_2$ readings, opens fully and the lungs will be allowed to deflate in order to offload $CO_2$, As seen in the ventilatory control of FIG. 6D, when the $ETCO_2$ is high enough, it will cause the expiratory flow to change.
  a) At time 652, the lung pressure begins to rise, the $ETCO_2$ is rising, and a relatively small amount of expiratory flow occurs according to expiratory flow setpoint 657. The inspiratory flow is at an inspiratory flow setpoint 659.
  b) At time 654, the high pressure setpoint 651 has been reached, and this causes the expiratory valve to open. The lung pressure falls. It is noted that the $ETCO_2$ amount is near the high $ETCO_2$ setpoint 655, but has not been exceeded.
  c) At time 656, the lung pressure is at the low pressure setpoint 653, and this causes the expiratory flow to drop to the expiratory flow setpoint 657. The lung pressure rises because the inspiratory flow rate is higher than the expiratory flow rate.
  d) At time 658, the $ETCO_2$ amount is at the high $ETCO_2$ setpoint 655 and this causes the expiratory valve to open. The valve stays open and allows the lung pressure to decline to near zero as the lung low pressure setpoint 653 is temporarily suspended. The lung is allowed to deflate, as seen by the long expiratory flow, in order to offload $CO_2$. The loss of volume and pressure are side effects of the fact that $CO_2$ is part of the air mixture, so air mixture must be blown out. The reason for opening the expiratory valve is not about lowering pressure, it is about lowering $CO_2$.
  e) At time 660, and the expiratory flow setpoint amount 657 is activated due to the decline in $ETCO_2$. This causes the expiratory flow to decline to the setpoint amount. The lung pressure rises. The time between times 660 and 662 is long enough to allow the lungs to re-inflate and pressurize.
  f) At time 662, the high pressure setpoint 651 has been reached, and this causes the expiratory valve to open. The lung pressure falls.
  g) The control continues with periodic increases in expiratory flow based on either the high lung pressure or high $ETCO_2$ measurements.

Typically, the pressure control continues as the primary control with potential periodic interruptions due to any high $ETCO_2$ measurements. Importantly, if there are too many interruptions, the inspiratory or expiratory setpoints should be modified.

The inspiratory flow is maintained at a constant level, but at a higher amount than the inspiratory flow setpoint 605 in FIG. 6A to compensate for the constant small expiratory flow of 657.

Overall, the periodic lung cycle in FIG. 6D may be longer than in FIG. 6A, primarily due to the lungs being allowed to inflate and deflate to a significant degree.

Per medical direction, a patient may be transitioned from the lung cycles shown in FIG. 6A to those shown in FIG. 6D which are inclusive of the FIG. 6A ventilator control, and also include the $ETCO_2$ trigger. At a later time, the patient may be switched back to the FIG. 6A control mode, and no longer utilize the $ETCO_2$ sensor and control of FIG. 6D.

However, if a spontaneous breath event occurs (pressure drop setpoint exceeded), the $ETCO_2$ control is superseded by the spontaneous breath control. In this case, the expiratory valve closes and the inspiratory valve is opened to the high flow setpoint 632 as shown in FIG. 6B at time 620b. Then the spontaneous breath control continues until time 628. Then the control is shifted back to $ETCO_2$ control.

For comparison to FIG. 6D, FIG. 7 shows a typical Capnographic Waveform for a typical breathing patient. This is the $ETCO_2$ readout from a $CO_2$ sensor in the expiration flow. The inspiration amount 701 is near zero as air goes into the lungs. The expiration amount of $ETCO_2$ 702 is shown and it slightly increases during lung exhale as the exchange of $O_2$ and $CO_2$ continues during the exhale period of the patent. The current reading $ETCO_2$ 703 is shown to the right of the chart for high visibility. A typical $ETCO_2$ reading is between 35-45 mm Hg. The higher waveform reading 702 is important for doctors, as it is an important number for understanding how well the lungs are functioning as $O_2$—$CO_2$ exchangers, and can indicate states of bronchospasm and other disease states.

Preferred Setpoints

Humans breathe in a tidal volume of air in a single breath. A breath is divided into inspiratory flow (inhale) and expiratory flow (exhale). In tidal ventilation the tidal volume must be delivered over the total inspiratory time frame for patient breathing to be normal. The expiratory flow occurs over a longer time at a inspiratory/expiratory ratio of about 1:2. For example: a tidal volume of 600 ml per breath at the rate of 20 breaths/min gives an average inspiratory volume rate of 0.6 L×20 breath/min=12 L/min. However, the flow rate during inspiration (only) is three times the average flow. This is typical for a physiologically normal person with a 20/40 second inspiration/expiration time per minute.

Conversely, a continuously flowing inspiration will deliver 12 L over sixty seconds at a constant flow of 0.2 L/sec during an entire minute, without simulating a patient's breath.

An operator is able to set the volume flow rate in L/min or ml/min. The result of either set variable will be the calculation and display of both (to two significant digits).

Preferably, to determine the amount of flow the patient needs, the operator inputs the patient's biological sex and height and software calculates Ideal body weight (IBW) via the Devine formula:
1. Man: Ideal Body Weight (kg)=50+2.3 kg per inch over 5 feet.
2. Woman: Ideal Body Weight (kg)=45.5+2.3 kg per inch over 5 feet.

In constant flow operators set a "rate and volume" for vent flow rate which is based on IBW. Even though the flow (in/out) to the lungs is continuous, it is operator friendly to show the setpoints in rate and volume/breath, similar to typical ventilator breathing modes:
Rate: 15 breaths/min
Volume/breath: 8 ml/kg IBW
For example: a 70" male patient with an IBW of 73 kg, and a chosen setpoint rate of 15 breaths/min will be:
Volume/breath: 73 kg*8 ml/kg=584 ml/breath
Volume/min: 0.584 L*15=8.76 L/min Preferably, the volume rate in both minutes and seconds are both shown, that is, 8.76 L/min and 146 ml/sec (i.e. 8760 ml/min/60). Since flow rate mode is continuous, the actual flowrate is a constant 8.76 L/min over the entire minute.

As another example, the operator sets the rate and volume independent of IBW: (e.g. rate 12 breaths/min, volume 500 ml/breath, which would be a volume display of 6 L/min and 100 ml/sec.

Both the rate and the volume are important to ventilator operators. The operator receives feedback of ventilating progress by monitoring the patient's oxygen level from a suitable patient blood oxygen readout on an operator display. Additionally, the amount of $CO_2$ in the expiratory flow is important to understand how well the lung functions by the exchange rate of oxygen into the blood.

In a preferred embodiment, the lung is set up with a minimum continuous inspiratory flow rate. The minimum flow rate (perhaps 100 ml/sec) is regulated by the inspiratory control valve. The operator watches, and adjusts the flow rate, until a desired minimum lung inflation pressure is reached and the $ETCO_2$ readings are within a normal range. As shown in FIGS. 1A and 2A, the internal flow within the lungs allows the inspiratory air to reach throughout the lungs.

The operation of the lung maintains a steady state condition if the $ETCO_2$, and the cardiovascular system operates within normal parameters.

Trigger setpoints for the expiratory control valve opening include:
a. Max/Min pressure setpoints. The operator sets an opening pressure setpoint and a closing pressure setpoint for the expiratory valve. Exemplary setpoints are opening the valve at 32 cm $H_2O$ and closing the valve at 2 cm $H_2O$. The expiratory valve then stays closed until the pressure reaches 32 cm $H_2O$, and so on. This creates a breathing pattern for the patient and is the main trigger method. The amount of flow is regulated by the inspiratory control valve. An exemplary setpoint is 100 ml/sec.
b. Optional Peak End Tidal Carbon Dioxide ($ETCO_2$) setpoint, which is used in conjunction with one or more other triggers. The $ETCO_2$ is measured by a sensor in the expiratory tube (not shown).
  i. Operator sets $ETCO_2$ Max setpoint (for example, 50 mm Hg). The expiratory valve remains open until the measured value is less than the setpoint value. Note: the operator may change the setpoint value while valve is open or closed and system will accept new setpoint.
c. Expiratory Pause (i.e. manual override by operator) which opens the expiratory control valve when the pause button is pushed down, and also closes the inspiratory valve).
d. When a maximum time setpoint is reached for an expiratory flow to happen (i.e. breath to be exhaled), this triggers the opening of the expiratory valve.

Alarm limits are displayed separately on an alarm screen.
1. Any value that can be set or measured may be associated with both high and low alarms.
2. Alarms are any of: visual, audio, or both on a per case basis.
3. Alarms are set prior to use and can be changed by the operator at any time
4. No ventilation starts without setting at least one alarm
5. This mode allows separate alarms when in-line nebulization of medications are given to the patient. The operator may change the alarms when the nebulizer is used.

While various embodiments of the present invention have been described, the invention may be modified and adapted to various operational methods to those skilled in the art. Therefore, this invention is not limited to the description and figure shown herein, and includes all such embodiments, changes, and modifications that are encompassed by the scope of the claims.

I claim:
1. A lung ventilator system, comprising:
an inspiratory tube configured to be disposed within an airway tube as part of an inspiratory line,
an inspiratory flow rate measuring device coupled with the inspiratory line, and the inspiratory line coupled to a source of inspiratory air;
an expiratory line configured to be disposed at least partially within the airway tube, the expiratory line further comprising: an expiratory flow rate measuring device and a lung pressure measuring device coupled with the expiratory line;
an expiratory tube coupled to the expiratory line, the expiratory tube disposed within the airway tube;
an inspiratory airway positioned between the airway tube and the expiratory tube, the inspiratory airway coupled to the inspiratory line;

an inspiratory control valve operable for adjusting a rate of inspiratory airflow through the inspiratory line to a patient lung;
an expiratory control valve operable for adjusting a rate of expiratory airflow through the expiratory line away from the patient lung; and
a ventilatory controller operable to provide continuous inspiratory flow through the inspiratory line while providing an intermittent expiratory flow from the patient through the expiratory tube to facilitate concurrent venting outflow;
wherein the ventilatory controller is configured to regulate a lung pressure cycle, comprising:
a) an inspiratory flow rate controlled to an inspiratory setpoint,
b) the inspiratory setpoint is at a low flow setting,
c) the expiratory control valve switches between open and closed according to:
i) the expiratory control valve is configured to open when said lung pressure is at or above a high pressure setpoint, and
ii) the expiratory control valve is configured to close when said lung pressure is at or below a low pressure setpoint,
whereby the ventilatory controller is configured to regulate the lung pressure between the high pressure setpoint and the low pressure setpoint with periodic expiratory flows.

2. The lung ventilator system of claim 1, wherein a low flow system curated by the lung ventilator system is lung-protective in a setting of or for the prevention of Acute Respiratory Distress Syndrome (ARDS).

3. The lung ventilator system of claim 2, wherein
the inspiratory flow rate of about 66.6 ml/sec to about 312.5 ml/sec is maintained by the lung ventilator system; and
a continuous low-flow/sec state is configured to avoid regional overdistension and achieve a homogeneous gas distribution.

4. The lung ventilator system of claim 1, wherein the ventilatory controller includes an $ETCO_2$ control comprising:
a) an $ETCO_2$ measurement device configured to measure an expiratory $ETCO_2$ amount and wherein the inspiratory flow rate is maintained at a constant level sufficient to compensate for a constant small expiratory flow required to monitor $CO_2$ in the expiratory flow,
b) the expiratory control valve is configured to substantially open when the expiratory $ETCO_2$ amount is at or above an $ETCO_2$ high setpoint, and
c) the expiratory control valve is configured to substantially close when the expiratory $ETCO_2$ amount is at or below an $ETCO_2$ low setpoint while the lung pressure is at or below the low pressure setpoint.

5. The lung ventilator system of claim 4, wherein the $ETCO_2$ high setpoint is about 30-70 mm of mercury (Hg) and/or the $ETCO_2$ low setpoint is about 20-50 mm of mercury (Hg).

6. The lung ventilator system of claim 1, further comprising an $ETCO_2$ sensor disposed within the expiratory line.

7. The lung ventilator system of claim 1, wherein the expiratory tube extends below a lower end of the airway tube.

8. The lung ventilator system of any of claim 1, wherein the airway tube comprises an endotracheal tube or a tracheostomy tube.

9. A lung ventilator system, comprising:
an inspiratory tube configured to be disposed within an airway tube as part of an inspiratory line, an inspiratory flow rate measuring device coupled with the inspiratory line, and the inspiratory line coupled to a source of inspiratory air;
an expiratory line configured to be disposed at least partially within the airway tube, the expiratory line further comprising: an expiratory flow rate measuring device and a lung pressure measuring device coupled with the expiratory line;
an expiratory tube coupled to the expiratory line, the expiratory tube disposed within the airway tube;
an inspiratory airway positioned between the airway tube and the expiratory tube, the inspiratory airway coupled to the inspiratory line;
an inspiratory control valve operable for adjusting a rate of inspiratory airflow through the inspiratory line to a patient lung;
an expiratory control valve operable for adjusting a rate of expiratory airflow through the expiratory line away from the patient lung; and
a ventilatory controller, wherein the ventilatory controller is configured to regulate a lung pressure cycle, comprising:
a) an inspiratory flow rate controlled to an inspiratory setpoint,
b) the inspiratory setpoint is at a low flow setting,
c) the expiratory control valve switches between open and closed according to:
i) the expiratory control valve is configured to open when said lung pressure is at or above a high pressure setpoint, and
ii) the expiratory control valve is configured to close when said lung pressure is at or below a low pressure setpoint,
whereby the ventilatory controller is configured to regulate the lung pressure between the high pressure setpoint and the low pressure setpoint with periodic expiratory flows; and
wherein the airway tube comprises an endotracheal tube or a tracheostomy tube.

10. The lung ventilator system of any of claim 9, further comprising an $ETCO_2$ sensor disposed within the expiratory line.

11. The lung ventilator system of claim 9, wherein the expiratory tube extends below a lower end of the airway tube.

12. The lung ventilator system of any of claim 9, wherein the ventilatory controller is operable to provide continuous inspiratory flow through the inspiratory line while providing an intermittent expiratory flow from the patient through the expiratory tube to facilitate concurrent venting outflow.

13. The lung ventilator system of claim 9, wherein a low flow system curated by the lung ventilator system is lung-protective in a setting of or for the prevention of Acute Respiratory Distress Syndrome (ARDS).

14. The lung ventilator system of claim 13, wherein
the inspiratory flow rate of about 66.6 ml/sec to about 312.5 ml/sec is maintained by the lung ventilator system; and
a continuous low-flow/sec state is configured to avoid regional overdistension and achieve a homogeneous gas distribution.

15. A lung ventilator system, comprising:
an inspiratory tube configured to be disposed within an airway tube as part of an inspiratory line, an inspiratory flow rate measuring device coupled with the inspiratory line, and the inspiratory line coupled to a source of inspiratory air;

an expiratory line configured to be disposed at least partially within the airway tube, the expiratory line further comprising: an expiratory flow rate measuring device and a lung pressure measuring device coupled with the expiratory line;

an expiratory tube coupled to the expiratory line, the expiratory tube disposed within the airway tube;

an inspiratory airway positioned between the airway tube and the expiratory tube, the inspiratory airway coupled to the inspiratory line;

an inspiratory control valve operable for adjusting a rate of inspiratory airflow through the inspiratory line to a patient lung;

an expiratory control valve operable for adjusting a rate of expiratory airflow through the expiratory line away from the patient lung; and a ventilatory controller, wherein the ventilatory controller is configured to regulate a lung pressure cycle, comprising:

a) an inspiratory flow rate controlled to an inspiratory setpoint, b) the inspiratory setpoint is at a low flow setting, c) the expiratory control valve switches between open and closed according to:
  i) the expiratory control valve is configured to open when said lung pressure is at or above a high pressure setpoint, and
  ii) the expiratory control valve is configured to close when said lung pressure is at or below a low pressure setpoint;

whereby the ventilatory controller is configured to regulate the lung pressure between the high pressure setpoint and the low pressure setpoint with periodic expiratory flows;

wherein a low flow system curated by the lung ventilator system is lung-protective in a setting of or for the prevention of Acute Respiratory Distress Syndrome (ARDS);

the inspiratory flow rate of about 66.6 ml/sec to about 312.5 ml/sec is maintained by the lung ventilator system; and a continuous low-flow/sec state is configured to avoid regional overdistension and achieve a homogeneous gas distribution.

16. The lung ventilator system of any of claim 15, wherein a ventilatory controller is operable to provide continuous inspiratory flow through the inspiratory line while providing an intermittent expiratory flow from the patient through the expiratory tube to facilitate concurrent venting outflow.

17. The lung ventilator system of claim 16, wherein the ventilatory controller includes an $ETCO_2$ control comprising:

a) an $ETCO_2$ measurement device configured to measure an expiratory $ETCO_2$ amount and wherein the inspiratory flow rate is maintained at a constant level sufficient to compensate for a constant small expiratory flow required to monitor $CO_2$ in the expiratory flow, b) the expiratory control valve is configured to substantially open when the expiratory $ETCO_2$ amount is at or above an $ETCO_2$ high setpoint, and c) the expiratory control valve is configured to substantially close when the expiratory $ETCO_2$ amount is at or below an $ETCO_2$ low setpoint while the lung pressure is at or below the low pressure setpoint.

18. The lung ventilator system of claim 17, wherein the $ETCO_2$ high setpoint is about 30-70 mm of mercury (Hg) and/or the $ETCO_2$ low setpoint is about 20-50 mm of mercury (Hg).

\* \* \* \* \*

UNITED STATES PATENT AND TRADEMARK OFFICE
CERTIFICATE OF CORRECTION

PATENT NO. : 11,833,304 B2
APPLICATION NO. : 17/196434
DATED : December 5, 2023
INVENTOR(S) : Adam D. Bell Page 1 of 1

It is certified that error appears in the above-identified patent and that said Letters Patent is hereby corrected as shown below:

In the Claims

In Claim 8, Column 19, Line 65, 'The lung ventilator system of any of claim 1,' should read – The lung ventilator system of claim 1. –

In Claim 10, Column 20, Line 43, 'The lung ventilator system of any of claim 9,' should read – The lung ventilator system of claim 9. –

In Claim 12, Column 20, Line 49, 'The lung ventilator system of any of claim 9,' should read – The lung ventilator system of claim 9. –

In Claim 16, Column 22, Line 12, 'The lung ventilator system of any of claim 15,' should read – The lung ventilator system of claim 15 –

In Claim 16, Column 22, Line 13, 'wherein a ventilatory....' should read – wherein the ventilatory.... –

Signed and Sealed this
Twenty-seventh Day of February, 2024

Katherine Kelly Vidal
*Director of the United States Patent and Trademark Office*